US011547791B2

(12) United States Patent
Schabbach et al.

(10) Patent No.: US 11,547,791 B2
(45) Date of Patent: Jan. 10, 2023

(54) MEDICAMENT DELIVERY DEVICE

(71) Applicant: Sanofi-Aventis Deutschland GMBH, Frankfurt am Main (DE)

(72) Inventors: Michael Schabbach, Frankfurt am Main (DE); Beate Franke, Frankfurt am Main (DE); Giuliano Pradel, Besana in Brianza (IT); Ilario Melzi, Milan (IT); Stefan Verlaak, Paderno d'Adda (IT); Andrew Nelson, Dallas, TX (US)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 959 days.

(21) Appl. No.: 16/336,273

(22) PCT Filed: Sep. 20, 2017

(86) PCT No.: PCT/EP2017/073723
§ 371 (c)(1),
(2) Date: Mar. 25, 2019

(87) PCT Pub. No.: WO2018/060025
PCT Pub. Date: Apr. 5, 2018

(65) Prior Publication Data
US 2019/0209774 A1    Jul. 11, 2019

(30) Foreign Application Priority Data

Sep. 27, 2016    (EP) ..................................... 16190882

(51) Int. Cl.
*A61M 5/142*    (2006.01)
*A61M 5/148*    (2006.01)
(Continued)

(52) U.S. Cl.
CPC ........ *A61M 5/14232* (2013.01); *A61M 5/148* (2013.01); *A61M 5/1483* (2013.01);
(Continued)

(58) Field of Classification Search
CPC ......... A61M 2005/14252; A61M 2005/14506; A61M 2005/206; A61M 2005/2073;
(Continued)

(56) References Cited

U.S. PATENT DOCUMENTS 3,786,683 A * 1/1974 Berman ................ B01L 3/0279
422/922
3,930,761 A * 1/1976 Barraclough ........ A61B 17/205
604/223
(Continued)

FOREIGN PATENT DOCUMENTS

CN    101631578    1/2010
CN    101801438    8/2010
(Continued)

OTHER PUBLICATIONS

International Search Report and Written Opinion in Application No. PCT/EP2017/073723, dated Nov. 30, 2017, 12 pages.
(Continued)

*Primary Examiner* — Quynh-Nhu H. Vu
(74) *Attorney, Agent, or Firm* — Fish & Richardson P.C.

(57) ABSTRACT

The present disclosure relates to a medicament delivery device. The medicament delivery device comprises a housing, a needle and a reservoir. The needle is configured to project from a distal end of the housing. The reservoir is disposed in the housing and has a flexible wall. The medicament delivery device further comprises a dispensing member and a biasing member. The dispensing member is disposed in the housing and the biasing member is configured to bias the dispensing member to move in an arcuate
(Continued)

path relative to the housing such that the dispensing member moves across the flexible wall of the reservoir to dispense medicament from the reservoir when the reservoir contains medicament.

16 Claims, 8 Drawing Sheets

(51) Int. Cl.
  *A61M 5/20* (2006.01)
  *A61M 5/145* (2006.01)
(52) U.S. Cl.
  CPC ...... *A61M 5/14248* (2013.01); *A61M 5/2033* (2013.01); *A61M 2005/14252* (2013.01); *A61M 2005/14256* (2013.01); *A61M 2005/14272* (2013.01); *A61M 2005/14506* (2013.01); *A61M 2005/206* (2013.01); *A61M 2005/2073* (2013.01)
(58) Field of Classification Search
  CPC .......... A61M 5/14232; A61M 5/14248; A61M 5/148; A61M 5/1483; A61M 5/2033
  See application file for complete search history.

(56) References Cited

U.S. PATENT DOCUMENTS

| | | | | |
|---|---|---|---|---|
| 4,070,725 | A * | 1/1978 | Austin et al. | B05B 9/0426 222/416 |
| 4,525,164 | A * | 6/1985 | Loeb | A61M 5/148 222/326 |
| 4,601,707 | A * | 7/1986 | Albisser | A61M 5/148 604/151 |
| 4,886,499 | A | 12/1989 | Cirelli et al. | |
| 5,441,490 | A | 8/1995 | Svedman | |
| 6,375,638 | B2 * | 4/2002 | Nason | A61M 5/148 604/153 |
| 6,626,329 | B2 * | 9/2003 | Rake | A61M 5/148 604/890.1 |
| 6,871,759 | B2 * | 3/2005 | Rake | A61M 5/148 604/890.1 |
| 2008/0228129 | A1 | 9/2008 | Kriesel et al. | |
| 2009/0028824 | A1 * | 1/2009 | Chiang | A61P 43/00 424/85.7 |
| 2010/0094219 | A1 | 4/2010 | Kriesel et al. | |
| 2012/0163999 | A1 | 6/2012 | Becker | |
| 2012/0323183 | A1 | 12/2012 | Peterson et al. | |

FOREIGN PATENT DOCUMENTS

| | | | | |
|---|---|---|---|---|
| CN | 103338796 | | 10/2013 | |
| CN | 104302333 | | 1/2015 | |
| EP | 0197179 | A1 * | 4/1985 | ............. A61M 5/14 |
| EP | 0197179 | | 10/1986 | |
| JP | S58-500003 | | 3/1983 | |
| JP | S63-164963 | | 7/1988 | |
| JP | H6-504215 | | 5/1994 | |
| WO | WO 82/03556 | | 10/1982 | |
| WO | WO 1992/011879 | | 7/1992 | |
| WO | WO 2007/107786 | | 9/2007 | |
| WO | WO 2008/024812 | | 2/2008 | |
| WO | WO 2009/013736 | | 1/2009 | |
| WO | WO 2013/153042 | | 10/2013 | |

OTHER PUBLICATIONS

International Preliminary Report on Patentability in Application No. PCT/EP2017/073723, dated Apr. 2, 2019, 8 pages.

* cited by examiner

MEDICAMENT DELIVERY DEVICE

CROSS REFERENCE TO RELATED APPLICATIONS

The present application is the national stage entry of International Patent Application No. PCT/EP2017/073723, filed on Sep. 20, 2017, and claims priority to Application No. EP 16190882.7, filed on Sep. 27, 2016, the disclosures of which are incorporated herein by reference.

TECHNICAL FIELD

The present disclosure relates to a medicament delivery device.

BACKGROUND

A variety of diseases exist that require regular treatment by injection of a medicament and such injections can be performed by using injection devices. Various injection devices for delivering injections of medicament are known in the art. Another type of injection pump that is gaining traction is the bolus injector device. Some bolus injector devices are intended to be used with relatively large volumes of medicament, typically at least 1 ml and may be a few ml. Injection of such large volumes of medicament can take some minutes or even hours. Such high capacity bolus injector devices can be called large volume devices (LVDs). Generally such devices are operated by the patients themselves, although they may also be operated by medical personnel.

SUMMARY

It is an object of the present disclosure to provide an improved medicament delivery device.

According to the present disclosure, there is provided a medicament delivery device comprising: a housing having a distal end; a needle configured to project from the distal end of the housing, wherein the distal end of the housing is configured to overlie an injection site of a patient; a reservoir disposed in the housing and having a flexible wall; a dispensing member disposed in the housing; and, a biasing member configured to bias the dispensing member to move in an arcuate path relative to the housing such that the dispensing member moves across the flexible wall of the reservoir to dispense medicament from the reservoir when the reservoir contains medicament.

The dispensing member may comprise a roller. The dispensing member is rolled across the flexible wall of the reservoir to dispense medicament which reduces the friction between the dispensing member and the flexible wall in comparison to if the dispensing member was dragged across the flexible wall. In one embodiment, the roller is configured to move along the arcuate path relative to the housing about a first rotational axis and is configured to roll about a second rotational axis that is at an angle to the first rotational axis. In one embodiment, the second rotational axis is substantially perpendicular to the first rotational axis.

In one embodiment, the reservoir comprises a flexible bag.

The biasing member may comprise a spring. Preferably, the spring is a spiral spring or a torsion spring.

The housing may comprise first and second portions that are rotatably coupled. In one embodiment, rotation of the first portion relative to the second portion resiliently deforms the biasing member such that the biasing member urges the dispensing member to move along the arcuate path relative to the housing. Therefore, the biasing member may be stored in a relaxed state and may be primed immediately prior to use by rotating the first portion relative to the second portion. This is advantageous because otherwise if the biasing member is stored in the primed state it will degrade over time such that the biasing force exerted on the dispensing member by the biasing member is reduced. In one embodiment, at least one of the first and second portions comprises a screw thread.

In one embodiment, the needle is moveable between a retracted position in which it is fully disposed within the housing and an extended position in which is projects from the distal end of the housing to inject a patient's skin in use. Thus, when the needle is stored in the retraced position it is protected by the housing and is prevented from harming the patient. Moreover, in use, the needle automatically enters the injection site of the patient such that the medicament delivery process is made easier.

In one embodiment, the medicament delivery device comprises a lock that is movable from a locked state, wherein the biasing member is prevented from moving the dispensing member along the arcuate path relative to the housing, and an unlocked state, wherein the biasing member is able to move the dispensing member along the arcuate path.

In one embodiment, the medicament delivery device comprises a flat surface, wherein the reservoir is compressed between the dispensing member and the flat surface when the dispensing member moves along the arcuate path.

In one embodiment, the distal end of the housing comprises an adhesive layer to attach the distal end to the patient's skin in use.

In one embodiment, the flexible wall is located between the distal end and the dispensing member when the dispensing member moves across the flexible wall.

In one embodiment, the housing comprises a central axis and the arcuate path of the dispensing member extends at least partially around the central axis of the housing.

The reservoir may contain medicament.

In one embodiment, the medicament delivery device is a large volume device.

According to the present disclosure, there is also provided a method of dispensing medicament from a medicament delivery device that has a housing, a needle, a dispensing member and biasing member disposed in the housing, and a reservoir disposed in the housing and having a flexible wall, the method comprising: positioning a distal end of the housing in proximity to an injection site of a patient, wherein the needle projects from the distal end into the injection site; and, releasing the biasing member to exert a force on the dispensing member such that the dispensing member moves in an arcuate path relative to the housing across the flexible wall of the reservoir to dispense medicament from the reservoir to the injection site.

These and other aspects of the disclosure will be apparent from and elucidated with reference to the embodiments described hereinafter.

BRIEF DESCRIPTION OF THE FIGURES

Embodiments will now be described, by way of example only, with reference to the accompanying drawings, in which.

DETAILED DESCRIPTION

Figure 1:
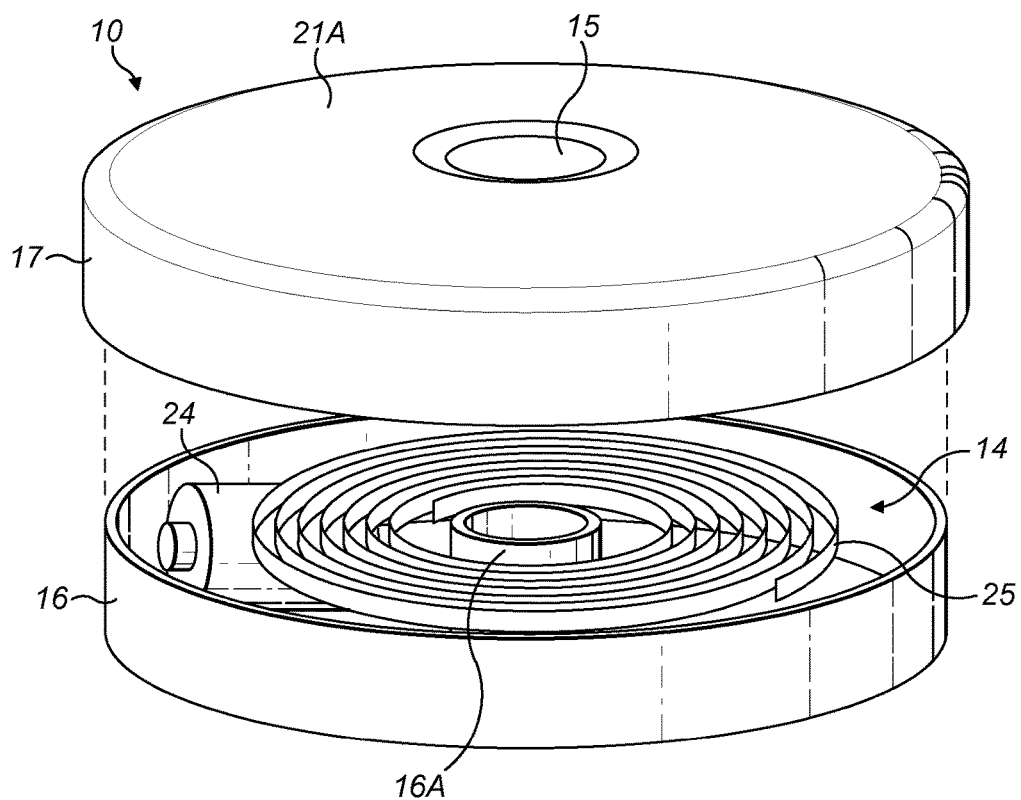
FIG. 1 is a schematic disassembled perspective view of a medicament delivery device according to a first embodiment.

A medicament delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for a large volume device). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

FIGS. 1 to 10 show a medicament delivery device 10, which in the exemplary embodiment comprises a bolus injector device, according to a first embodiment. The medicament delivery device 10 may be in the form of a large volume device.

The medicament delivery device 10 comprises a housing 11, a needle 12 and a medicament delivery mechanism comprising a needle actuating mechanism 13 and a dispensing mechanism 14. The medicament delivery device 10 further comprises an actuator 15 that is moveable relative to the housing 11.

The housing 11 comprises a distal portion 16 and a proximal portion 17. The term "distal" refers to a location that is relatively closer to a site of injection and the term "proximal" refers to a location that is relatively further away from the injection site.

The distal portion 16 of the housing 11 comprises a cylindrical peripheral wall 18 and an end wall 19 that together have a generally U-shaped cross-section. The distal portion 16 of the housing 11 further comprises a cylindrical internal wall 16A that is arranged concentrically with the cylindrical peripheral wall 18 of the distal portion 16. The proximal portion 17 of the housing 11 comprises a cylindrical peripheral wall 20 and an end wall 21 that together have a generally U-shaped cross-section. The proximal portion 17 of the housing 11 comprises a cylindrical internal wall 17A that is arranged concentrically with the cylindrical peripheral wall 20 of the proximal portion 17.

The peripheral wall 18 of the distal portion 16 of the housing 11 is slidably received in the peripheral wall 20 of the proximal portion 17 such that the end wall 19 of the distal portion 16 is spaced from the end wall 21 of the proximal portion 17 and a recess 22 is formed therebetween. The distal and proximal portions 16, 17 of the housing 11 together form a generally cylindrical shape that has a central axis (see the dashed line A-A in FIGS. 2 and 7).

The end wall 19 of the distal portion 16 has an outer surface 19A and an inner surface 19B and the end wall 21 of the proximal portion 17 has an outer surface 21A and an inner surface 21B. One or both of the outer surfaces 19A, 21A of the end walls 19, 21 of the distal and proximal portions 16, 17 may be substantially flat.

The outer surface 19A of the end wall 19 of the distal portion 16 comprises an adhesive layer (not shown) that is initially covered by a label (not shown). In use, the label is removed from the adhesive layer and then the adhesive layer is stuck to the patient's skin at the injection site of the patient such that the end wall 19 of the distal portion 16 is adhered to the injection site.

The dispensing mechanism 14 comprises a medicament reservoir 23, a dispensing member 24, a dispensing biasing member 25 and a dispensing lock (not shown).

The medicament reservoir 23 is in the form of a flexible bag 23. The flexible bag 23 is disposed in the recess 22 in the housing 11 and abuts the inner surface 19B of the end wall 19 of the distal portion 16.

The flexible bag 23 has a first end 23A and a second end 23B. The wall 26 of the flexible bag 23 is deformable. The flexible bag 23 extends at least partially about the central axis A-A of the housing 11. The flexible bag 23 may, for example, be C-shaped or U-shaped.

The flexible bag 23 is fluidly connected to an aperture 18A in the peripheral wall 18 of the distal portion 16. The aperture 18A forms a filling port 18A that allows for the flexible bag 23 to be filled with medicament through the peripheral wall 18 of the distal portion 16. The flexible bag 23 and/or the aperture 18A may comprise a one-way valve (not shown) that is configured to prevent medicament from flowing out of the flexible bag 23 via the aperture 18A. Alternatively, or additionally, a bung (not shown) may be provided that is inserted into the aperture 18A to seal the aperture 18A after the flexible bag 23 has been filled with medicament.

The dispensing member 24 is in the form of a roller 24. The roller 24 may be cylindrical. The roller 24 is disposed in the recess 22 in the housing 11 such that the flexible bag 23 is located between the roller 24 and the inner surface 19B of the end wall 19 of the distal portion 16. The roller 24 is configured to move about a first rotational axis in an arcuate path (shown by arrow 'X' in FIG. 9) from the first end 23A to the second end 23B of the flexible bag 23. The first rotational axis may be common with the central axis A-A of the housing 11.

Figure 2:
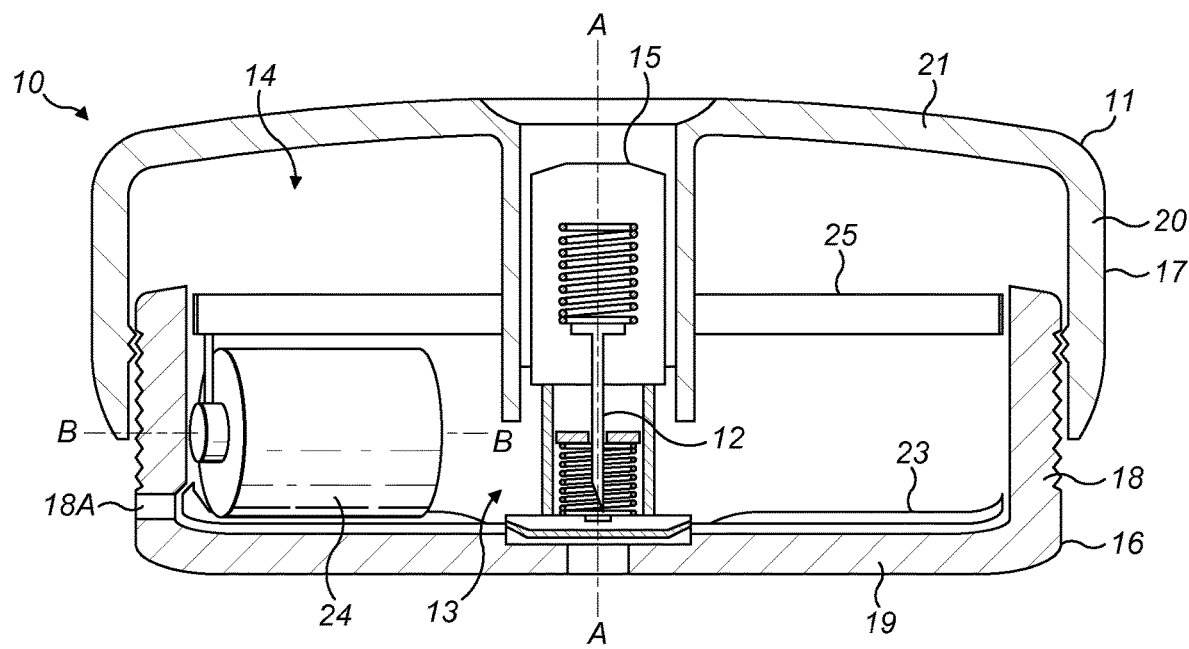
FIG. 2 is a schematic cross-sectional side view of the medicament delivery device of FIG. 1, wherein a proximal portion of the housing is in an initial position and a flexible bag is empty.
Figure 7:
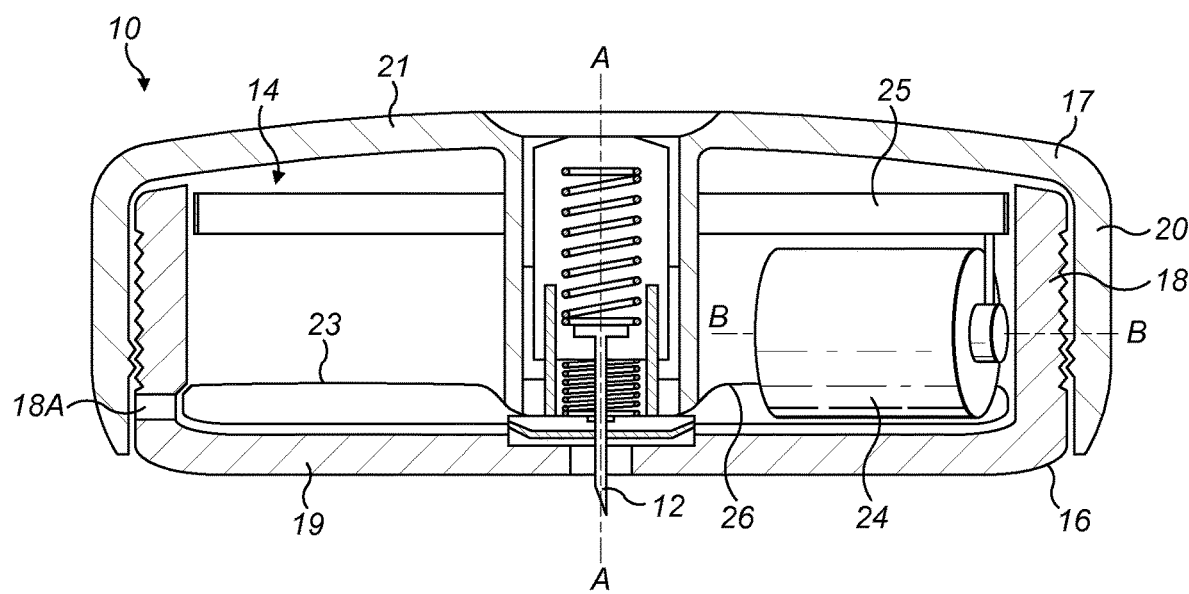
FIG. 7 is a schematic cross-sectional side view of the medicament delivery device of FIG. 1, wherein a dispensing mechanism is operated to dispense medicament from the flexible bag.
Figure 8:
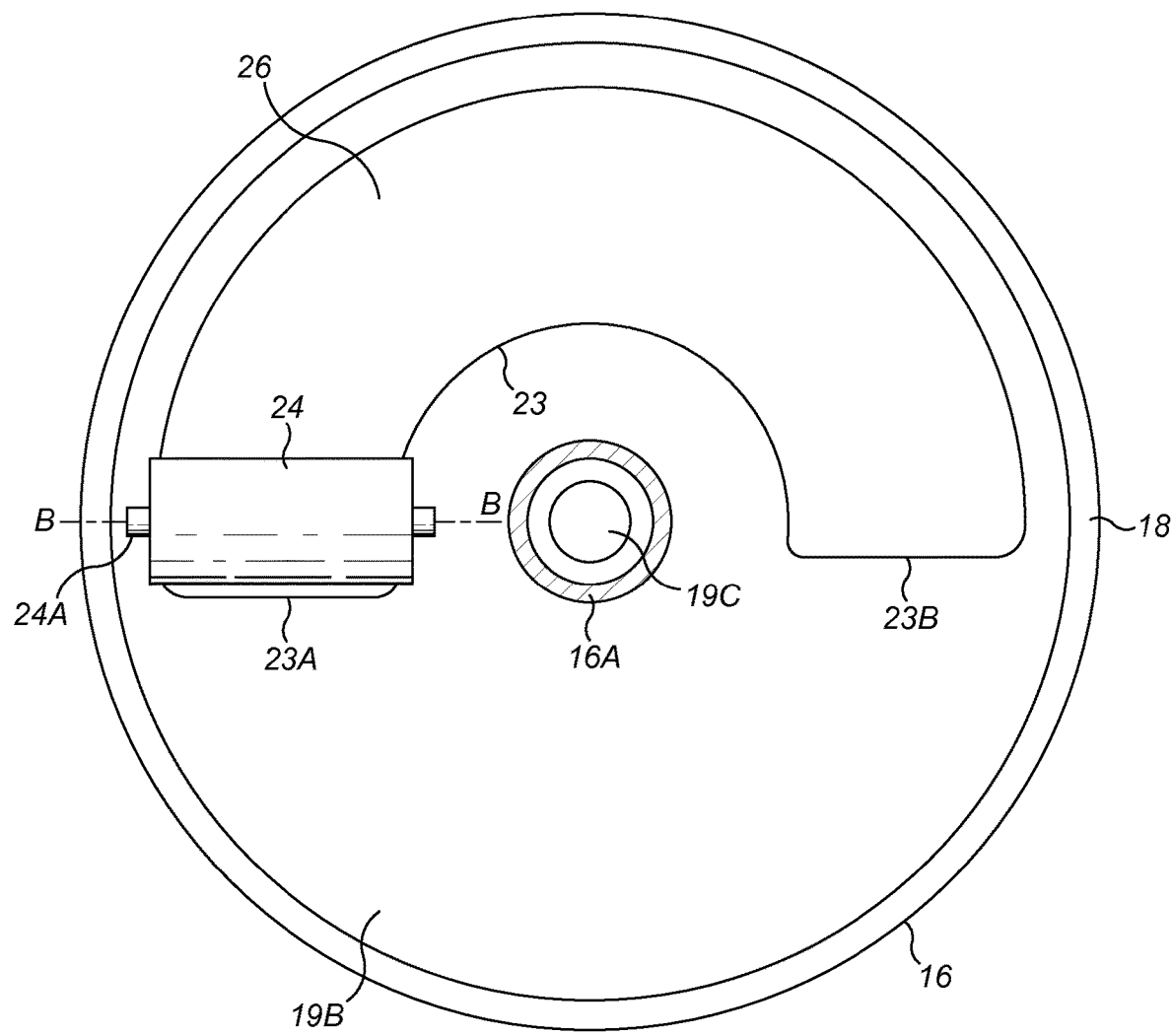
FIG. 8 is a schematic top view of a distal portion of the medicament delivery device of FIG. 1, wherein a roller is located at a first end of the flexible bag.

The roller 24 is rotatably coupled to an axle 24A configured such that the roller 24 is able to roll about a second rotational axis (shown by the dashed line B-B in FIGS. 2, 7 and 8). The second rotational axis B-B is at an angle to the central axis A-A. The roller 24 may be configured to roll about a second rotational axis B-B that is perpendicular to the central axis A-A.

In one embodiment, the axle 24A is moveably mounted to the housing 11. For example, the peripheral wall 18 of the distal portion 16 of the housing 11 may comprise a rail (not shown) and an end of the axle 24A may be mounted to the rail to slide along the rail when the roller 24 rolls about the second rotational axis B-B. In another embodiment (not shown), the axle 24A is coupled to the internal wall 16A of the distal portion 16 or the internal wall 17A of the proximal portion 17 via a bearing. In yet another embodiment, the axle 24A is not mounted to the housing 11.

The dispensing biasing member 25 is in the form of a dispensing spring 25. In the present embodiment, the dispensing spring 25 is a spiral spring 25. In an alternative embodiment (not shown), the dispensing member 25 comprises a different type of spring, for example, a torsion spring. In another embodiment (not shown), the dispensing biasing member 25 comprises a portion of resilient material that is twisted to exert a biasing force on the dispensing member 24.

The spiral spring 25 is disposed in the recess 22 in the housing 11 and extends about the central axis A-A of the housing 11. The spiral spring 25 is positioned between the internal wall 17A of the proximal portion 17 and the peripheral wall 18 of the distal portion 16.

A first end 51 of the spiral spring 25 is fixed to the internal wall 17A of the proximal portion 17 via a connecting member 52. A second end 53 of the spiral spring 25 is coupled to the axle 24A of the roller 24. In the present embodiment, the second end of the spiral spring 25 is coupled to the axle 24A of the roller 24A by a connecting member 27. However, in an alternative embodiment the connecting member 27 is omitted and instead the second end of the spiral spring 25 is connected directly to the axle 24A of the roller 24.

The medicament delivery device 10 further comprises a coupling 28 between the distal and proximal portions 16, 17 of the housing 11. The coupling 28 comprises first and second screw threads 29, 30. The first screw thread 29 is formed in the inner surface of the peripheral wall 20 of the proximal portion 17. The second screw thread 30 is formed in the outer surface of the peripheral wall 18 of the distal portion 16.

The first and second screw threads 29, 30 are configured to engage to couple the distal and proximal portions 16, 17 of the housing 11 such that the proximal portion 17 can be screwed to the distal portion 16 of the housing 11. Therefore, the proximal portion 17 is moveable from an initial position (shown in FIGS. 2 and 3), wherein the proximal portion 17 is coupled to the distal portion 16 such that the end walls 19, 21 of the distal and proximal portions 16, 17 are spaced apart, to a primed position (shown in FIGS. 4, 6, 7 and 10), wherein the proximal portion 17 is twisted relative to the distal portion 16 such that the screw threads 29, 30 engage and thus the end walls 19, 21 of the distal and proximal portions 16, 17 are moved closer together.

When the proximal portion 17 is in the initial position, the spiral spring 25 is in a natural state such that substantially no biasing force is exerted on the roller 24 by the spiral spring 25.

When the proximal portion 17 is moved to the primed position, the internal wall 17A of the proximal portion 17, and thus the first end of the spiral spring 25 attached thereto, is rotated relative to the distal portion 16. The dispensing lock (not shown) is initially in a locked state to retain the roller 24 in position relative to the distal portion 16 when the proximal portion 17 is moved from the initial position to the primed position. Thus, the second end of the spiral spring 25, which is coupled to the roller 24 by the connecting member 27, is retained in position relative to the distal portion 16 by the dispensing lock. Therefore, when the proximal portion 17 is moved from the initial position to the proximal position, the first end of the spiral spring 25 is rotated relative to the second end of the spiral spring 25 such that the spiral spring 25 is coiled to exert a biasing force on the roller 24. The biasing force urges the roller 24 to move along the arcuate path X relative to the housing 11. However, the dispensing lock initially prevents movement of the roller 24 along the arcuate path X.

The dispensing lock comprises a dispensing locking member (not shown) that is connected to the distal portion 16 of the housing 11 by a pivotal coupling. The dispensing locking member comprises an elongate member and a projection that is integrally formed with the elongate member.

The elongate member has first and second ends. The elongate member is attached to the pivotal coupling towards the first end of the elongate member. The second end of the elongate member is spaced from the pivotal coupling such that the second end is pivotable about the pivotal coupling. The pivotal coupling couples the locking member to the internal wall 16A of the distal portion 16.

The projection extends at an angle from the elongate member and is located proximate to the first end of the elongate member. The elongate member and projection may be arranged such that the dispensing locking member is generally L-shaped or V-shaped.

The dispensing locking member is moveable from a locked state to an unlocked state. In the locked state, the dispensing locking member is positioned such that the elongate member extends radially outwardly, in the direction away from the central axis A-A of the housing 11, to abut the roller 24 such that the roller 24 is prevented from moving along the arcuate path X. Moreover, in the locked state, the dispensing locking member is positioned such that the projection extends towards the end wall 21 of the proximal portion 17 at an angle towards the central axis A-A of the housing 11.

The dispensing locking member is moveable to the unlocked state, wherein the dispensing locking member is rotated such that the second end of the elongate member and the projection pivot about the pivotal couplings to move radially inwardly towards the central axis A-A of the housing 11. When the dispensing locking member is in the unlocked state, the second end of the elongate member is spaced from the roller 24 such that the dispensing locking member does not abut the roller 24. Therefore, the roller 24 is not restricted from moving relative to the housing 11 along the arcuate path X by the dispensing locking member.

The actuator 15 is in the form of a button 15 that has a peripheral wall 15A and an end wall 15B. The button 15 is received in the proximal portion 17 of the housing 11 such that the peripheral wall 15A of the button 15 is located on the inside of the internal wall 17A of the proximal portion 17 and is concentrically aligned therewith. The button 15 is slidable within the internal wall 17A of the proximal portion 17 in the direction of the central axis A-A of the housing 11.

Figure 6:
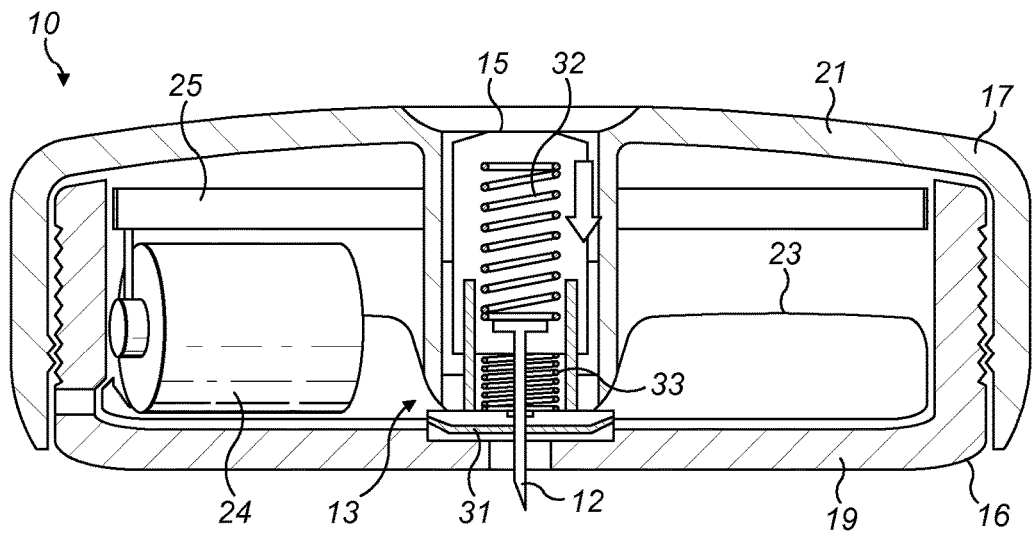
FIG. 6 is a schematic cross-sectional side view of the medicament delivery device of FIG. 1, wherein the needle is in an extended position.

The needle 12 is moveable relative to the distal portion 16 of the housing 11 between a retracted position (shown in FIGS. 2 to 4, and 10) and an extended position (shown in FIGS. 6 and 7). When the needle 12 is in the retracted position, the needle 12 is fully received in the recess 22 in the housing 11 such that the needle 12 is shielded to prevent damage to the needle 12 and to protect the patient from being accidentally injured by the needle 12.

When the needle 12 is moved from the retracted position to the extended position, the needle 12 is moved linearly in the direction of the central axis A-A of the housing 11 such that the end of the needle 12 projects out of an aperture 19C in the end wall 19 of the distal portion 16. Thus, when the adhesive layer of the distal portion 16 is adhered to the injection site of a patient, the needle 12 pierces the patient's skin to extend into the injection site to deliver medicament thereto.

The medicament delivery device 10 further comprises a septum 31 that is fixed to the inner surface 19B of the end wall 19 of the distal portion 16. The septum 31 is located over the aperture 19C in the end wall 19 of the distal portion 16. The needle 12, which is initially in the retracted position, is protected by the septum 31. More specifically, the septum 31 prevents the ingress of contaminants through the aperture 19C in the end wall 19 of the distal portion 16 and into contact with the sterile needle 12. When the needle 12 is moved to the extended position, the needle 12 pierces the septum 31 and the end of the needle 12 passes through the septum 31 to project from the end wall 19. The septum 31 may be manufactured from an impermeable material such as plastic, rubber or metal foil. In alternative embodiments, the septum 31 is fixed to the outer surface 19A of the end wall 19 of the distal portion 16 or is located in the aperture 19C in the end wall 19.

The needle actuating mechanism 13 comprises needle extension and retraction biasing members 32, 33, extension and retraction holding elements 34, 35, a needle extension lock 36 and a needle retraction lock (not shown).

The needle extension biasing member 32 is in the form of a needle extension spring 32. The needle extension spring 32 may be a helical spring. The needle extension spring 32 is located inside the peripheral wall 15A of the button 15 and extends about the central axis A-A of the housing 11. The needle extension spring 32 is disposed between a base 12A of the needle 12 and the extension holding element 34.

The extension holding element 34 is fixed relative to the distal portion 16 of the housing 11 and is located on the opposite side of the base 12A of the needle 12 to the septum 31. The extension holding element 34 is configured to act as a stop against which the proximal end of the needle extension spring 32 abuts such that the proximal end of the needle extension spring 32 is prevented from moving towards the end wall 21 of the proximal portion 17 in the direction of the central axis A-A of the housing 11. When the needle 12 is in the initial retracted position, the needle extension spring 32 is compressed between the base 12A of the needle 12 and the extension holding element 34 such that the needle extension spring 32 urges the needle 12 away from the extension holding element 34 in the direction of the central axis A-A of the housing 11 such that the needle 12 is biased to move into the extended position.

The needle extension lock 36 comprises an extension locking member 38 that is connected to the distal portion 16 of the housing 11 by a pivotal coupling 39. The extension locking member 38 comprises an elongate member 38A and first and second projections 40, 41 that are integrally formed with the elongate member 38A. The first projection 40 is located at the distal end of the elongate member 38A and the second projection 41 is located towards the proximal end of the elongate member 38A.

The elongate member 38A is attached to the pivotal coupling 39 at a point between the proximal and distal ends of the elongate member 38A such that the first and second projections 40, 41 are pivotable about the pivotal coupling 39.

Figure 5:
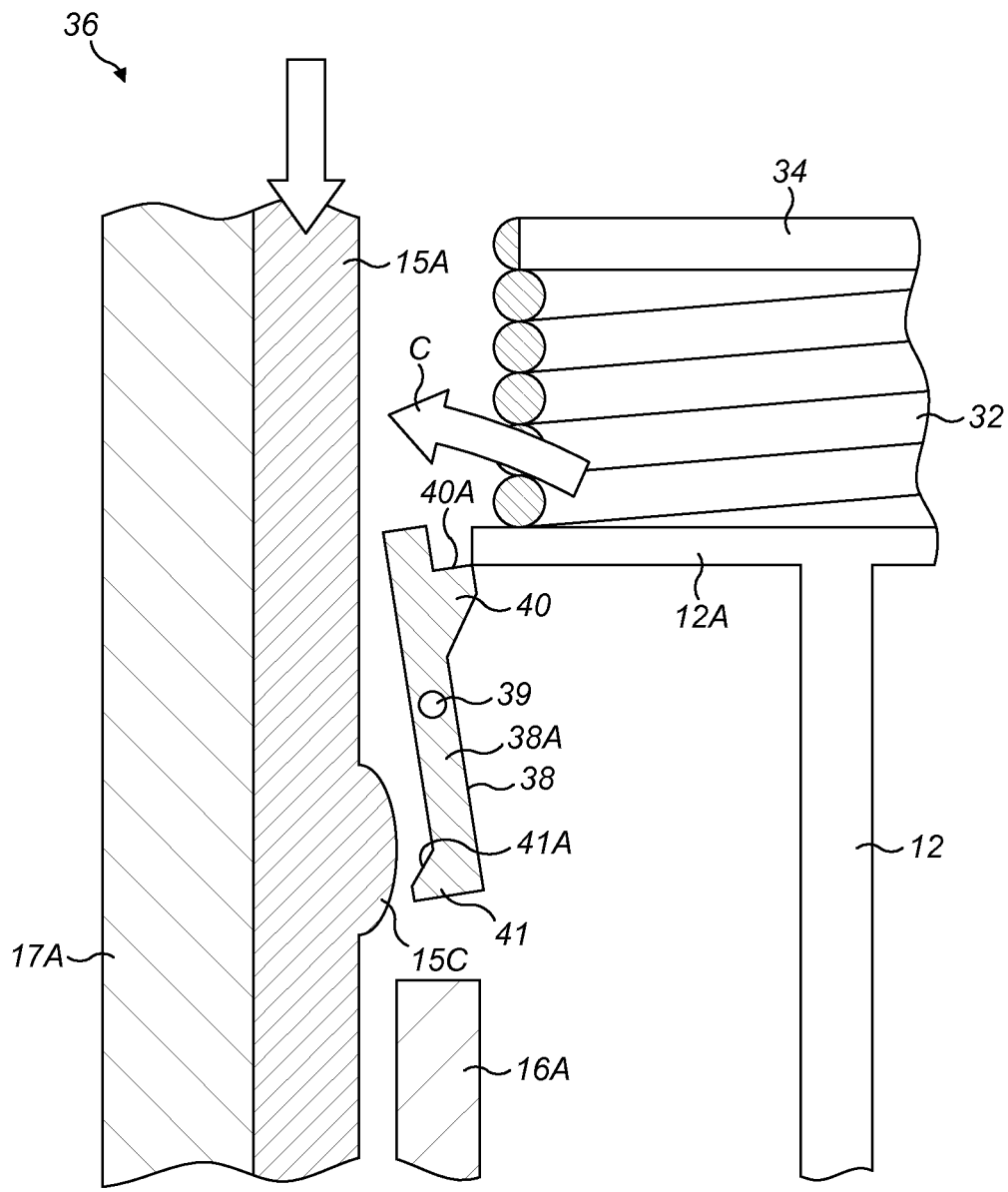
FIG. 5 is a close-up schematic cross-sectional side view of a needle extension lock of the medicament delivery device of FIG. 1, wherein a needle locking member is moved to an unlocked state.

The extension locking member 38 is moveable from a locked state to an unlocked state (as shown in FIG. 5). In the locked state, the extension locking member 38 is positioned such that the elongate member 38A extends substantially parallel to the central axis A-A of the housing 11 and the first projection 40 of the extension locking member 38 is located nearer to the end wall 21 of the proximal portion 17 of the housing 11 than the second projection 41.

The first projection 40 of the extension locking member 38 extends radially inwardly towards the central axis A-A of the housing 11 when the extension locking member 38 is in the locked state. The first projection 40 comprises a proximal-facing surface 40A that abuts the base 12A of the needle 12 when the extension locking member 38 is in the locked state such that movement of the needle 12 in the direction of the central axis A-A of the housing 11 towards the end wall 19 of the distal portion 16 is prevented. Thus, when the extension locking member 38 is in the locked state, the extension locking member 38 retains the needle 12 in the retracted position against the force of the needle extension spring 32, which is held in a compressed state between the base 12A of the needle 12 and the extension holding element 34.

The second projection 41 of the extension locking member 38 extends radially outwardly away from the central axis A-A of the housing 11 when the extension locking member 38 is in the locked state. The second projection 41 comprises an angled surface 41A that faces at an angle away from the central axis A-A of the housing 11 and towards the end wall 21 of the proximal portion 17.

The button 15 comprises a lip 15C that extends radially inwardly from the inside of the peripheral wall 15A of the button 15 in the direction towards the central axis A-A of the housing 11. The lip 15C may be generally annular.

The lip 15C of the button 15 is configured to abut the angled surface 41A of the extension locking member 38 when the button 15 is moved within the housing 11 towards the end wall 19 of the distal portion 16. This causes the second projection 41 of the extension locking member 38 to be urged radially inwardly towards the central axis A-A such that the extension locking member 38 is rotated from the locked state to the unlocked state (in the direction of arrow 'C' in FIG. 5). In the unlocked state, the first projection 40 is moved radially outwardly such that it no longer abuts the base 12A of the needle 12 and therefore the base 12A of the needle 12 is able to move away from the extension holding element 34 under the force of the needle extension spring 32. Thus, when the extension locking member 38 is in the unlocked state, the needle 12 moves from the retracted position to the extended position under the force of the needle extension spring 32.

The needle retraction biasing member 33 is in the form of a needle retraction spring 33. The needle retraction spring 33 may be a helical spring. The needle retraction spring 33 is located inside the distal portion 16 of the housing 11 and extends about the central axis A-A thereof. The needle retraction spring 33 is disposed between the retraction holding element 35 and the septum 31. The septum 31 is fixed relative to the distal portion 16 of the housing 11 and therefore acts as a stop against which the distal end of the needle retraction spring 33 abuts. Alternatively, the needle retraction spring 33 may abut the end wall 19 of the distal portion 16.

The retraction holding element 35 is slidably received in the internal wall 16A of the distal portion 16 of the housing 11. The needle retraction spring 33 is initially compressed between the septum 31 and the retraction holding element 35 such that the needle retraction spring 33 urges the retraction holding element 35 away from the septum 31 in the direction of the central axis A-A of the housing 11. The needle retraction lock (not shown) initially retains the retraction holding element 35 in position against the force of the needle retraction spring 33 such that the needle retraction spring 33 is compressed.

The needle retraction lock comprises a retraction locking member (not shown) that is connected to the distal portion 16 of the housing 11 by a pivotal coupling (not shown). The retraction locking member comprises first and second elongate members and a projection. The first and second elongate members are integrally formed at one end. The first and second elongate members extend at an angle to each other. The first and second elongate members may extend substantially perpendicular to each other.

The first and second elongate members comprise respective free ends that are remote to the pivotal coupling. The projection is located at the free end of the second elongate member.

The retraction locking member is pivotable from a locked state to an unlocked state. In the locked state, the retraction locking member is positioned such that the first elongate member extends radially outwardly away from the central axis A-A of the housing 11 and, in one embodiment, is substantially perpendicular to the central axis A-A of the housing 11. The free end of the first elongate member is located at, or near to, the second end 23B of the flexible bag 23. Moreover, in the locked state, the retraction locking member is positioned such that the second elongate member extends towards the end wall 21 of the proximal portion 17 from the pivotal coupling and, in one embodiment, is substantially parallel to the central axis A-A of the housing 11.

When the retraction locking member is in the locked state, the projection of the retraction locking member extends radially inwardly towards the central axis A-A of the housing 11 to abut a proximal-facing surface of the retraction holding element 35. Thus, the retraction holding element 35 is prevented from moving towards the end wall 21 of the proximal portion 17 and thus the needle retraction spring 33 is held in a compressed state between the septum 31 and the retraction holding element 35.

Movement of the roller 24 along the arcuate path X within the housing 11 to the second end 23B of the flexible bag 23 causes the roller 24 to be urged against the free end of the first elongate member. Thus, movement of the roller 24 to the second end 23B of the flexible bag 23 results in a force being exerted on the free end of the first elongate member. This force causes the free end of the first elongate member to be urged towards the end wall 19 of the distal portion 16 such that the retraction locking member is urged to rotate about the pivotal coupling from the locked state to the unlocked state.

When the retraction locking member is rotated to the unlocked state, the projection at the free end of the second elongate member is moved radially outwardly away from the central axis A-A of the housing 11 such that the projection is spaced from the retraction holding element 35. Thus, the projection no longer hold the retraction holding element 35 in place against the force of the needle retraction spring 33 and so the retraction holding element 35 is moved towards the end wall 21 of the proximal end 17 by the needle retraction spring 33.

The needle 12 extends through an aperture 35A in the retraction holding element 35 such that when the needle 12 is in the extended position and the retraction locking member is in the locked state the base 12A of the needle 12 is located in proximity to the retraction holding element 35. Thus, when the retraction locking member is subsequently moved to the unlocked state, the retraction holding element 35 is released such that the needle retraction spring 33 urges the retraction holding element 35 against the base 12A of the needle 12 to move the needle 12 towards the end wall 21 of the proximal portion 17 and into the retracted position.

A clearance gap (not shown) may be provided between the retraction locking member and the septum 31 and end wall 19 of the distal portion 16 to facilitate movement of the retraction locking member between the locked and unlocked states. Alternatively, the septum 31 may be manufactured from a flexible material that facilitates movement of the retraction locking member.

An exemplary operation of the medicament delivery device 10 will now be described. The medicament delivery device 10 is typically stored in a sterile packaging (not shown). The patient first removes the medicament delivery device 10 from the sterile packaging. When the medicament delivery device 10 is removed from the sterile packaging the proximal portion 17 of the housing 11 is in the initial position, the needle 12 is in the retracted position, and the button 15 is retracted into the proximal portion 17 (as shown in FIG. 2) such that the patient is not able to access the button 15 to actuate the button 15. For example, the inner dimension of the internal wall 17A of the proximal portion 17 may be sufficiently small that the patient is not able to insert a finger into the internal wall 17A to access the button 15. Thus, the patient is not able to depress the button 15 to operate the dispensing mechanism 14 to dispense medicament from the flexible bag 23 and thus the dispensing mechanism 14 is rendered inoperable. Moreover, the patient is not able to operate the needle actuating mechanism 13 to move the needle 12 to the extended position.

Figure 3:
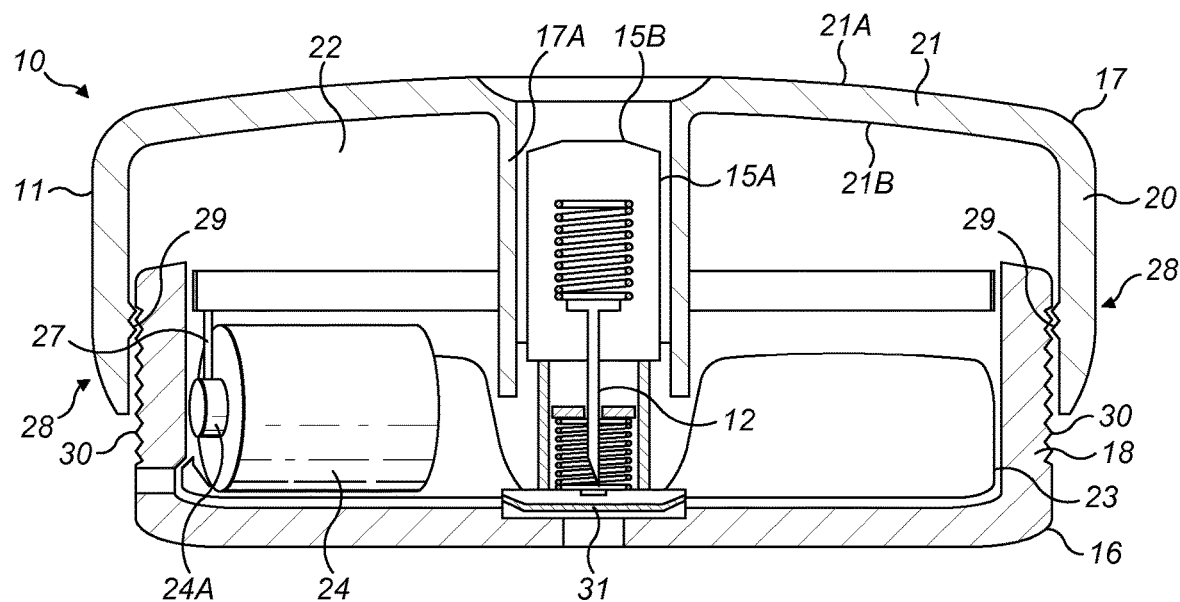
FIG. 3 is a schematic cross-sectional side view of the medicament delivery device of FIG. 1, wherein the proximal portion of the housing is in the initial position and the flexible bag is filled with medicament.

The patient then supplies medicament to the dispensing mechanism 14 of the medicament delivery device 10. More specifically, the patient supplies medicament to the flexible bag 23 via the filling port 18A in the peripheral wall 18 of the distal portion 16 of the housing 11 such that the flexible bag 23 is filled with medicament (as shown in FIG. 3). The medicament may be supplied from, for example, a syringe, container, or pressurised canister. In an alternative embodiment, the medicament reservoir 23 is pre-filled with medicament, in which case the filling port 18A may be omitted.

Next, the label (not shown) is removed from the adhesive layer (not shown) on the outer surface 19A of the end wall 19 of the distal portion 16. The adhesive layer is then adhered to the patient's skin at the injection site such that the end wall 19 of the distal portion 16 is secured to the injection site.

Figure 4:
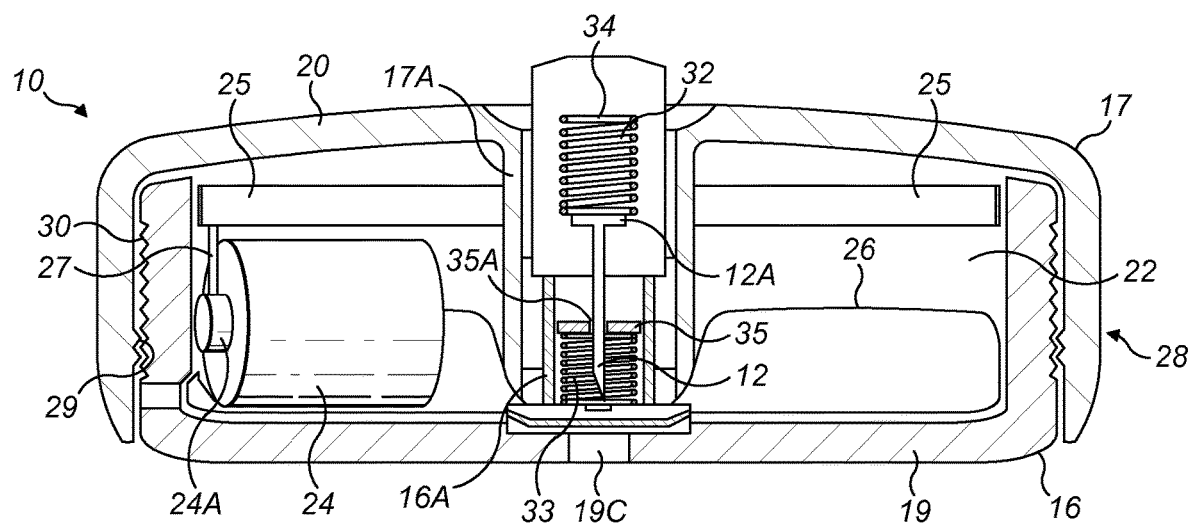
FIG. 4 is a schematic cross-sectional side view of the medicament delivery device of FIG. 1, wherein the proximal portion is in a primed position and a needle is in a retracted position.

The patient then rotates the proximal portion 17 relative to the distal portion 16 such that the engagement of the first and second screw threads 62, 63 causes the proximal portion 17 to move from the initial position to the primed position (as shown in FIG. 4). For example, the patient may use one hand to apply a force to the proximal portion 17 to twist the proximal portion 17 relative to the distal portion 16. The rotation of the proximal portion 17 relative to the distal portion 16 causes the proximal portion 17 to move relative to the distal portion 16 in the direction of the central axis A-A of the housing 11 such that the end wall 21 of the proximal portion 17 moves towards the end wall 19 of the distal portion 16.

As the proximal portion 17 is moved to the primed position, the first end of the spiral spring 25, which is attached to the internal wall 17A of the proximal portion 17, is moved relative to the second end of the spiral spring 24, which is attached to the initially stationary roller 24, such that the spiral spring 25 is coiled to exert a biasing force on the roller 24. The biasing force urges the roller 24 to move along the arcuate path X relative to the housing 11. The dispensing locking member of the dispensing mechanism 14 is initially in the locked state to hold the roller 24 in position against the force of the spiral spring 25.

When the proximal portion 17 reaches the primed position, the proximal portion 17 is retained in the primed position by the engagement of the first and second screw threads 29, 30. The coiled spiral spring 25 urges the proximal portion 17 to rotate relative to the distal portion 16, in the opposite direction to which the proximal portion 17 was rotated from the initial position to the proximal position, such that the proximal portion 17 is biased away from the primed position by the force of the spiral spring 25. However, the configuration of the first and second screw threads 29, 30 is such to prevent the proximal portion 17 from moving away from the primed position under the force of the spiral spring 25. This may be achieved, for example, due to the pitch of the first and second screw threads 29, 30 or alternatively by a latch or locking members that engage to hold the proximal portion 17 in position relative to the distal portion 16. Therefore, once the patient has moved the proximal portion 17 to the primed position the patient no longer needs to apply a force to the proximal portion 17 to retain the proximal portion 17 in the primed position.

The button 15 is received in the internal wall 17A of the proximal portion 17 of the housing 11 such that when the proximal portion 17 is moved to the primed position, and thus the end wall 21 of the proximal portion 17 is moved towards the end wall 19 of the distal portion 16, the proximal portion 17 slides relative to the button 15. This causes the button 15 to project from the proximal portion 17 (as shown in FIG. 4). Therefore, the button 15 may be actuated by the patient. The button 15 projects from the end wall 21 of the proximal portion 17 when the proximal portion 17 is in the primed position.

With the proximal portion 17 in the primed position, the medicament delivery device 10 is primed for supplying medicament to the injection site of the patient. The patient depresses the end wall 15B of the button 15 such that the button 15 is slid into the proximal portion 17 of the housing 11. This causes the button 15 to engage with the needle extension lock 36 such that the needle extension spring 32 is released to move the needle 12 to the extended position. In more detail, the button 15 is slid towards the end wall 19 of the distal portion 16 until the projection 15C of the button 15 is urged against the angled surface 41A of the second projection 41 of the extension locking member 38, resulting in the extension locking member 38 rotating from the locked state to the unlocked state (as shown in FIG. 5). As discussed above, this allows the base 12A of the needle 12 to move away from the extension holding element 34 under the force of the needle extension spring 32 such that the needle 12 moves axially to pass through the septum 31 to extend out of the aperture 19C in the end wall 19 of the distal portion 16. Thus, the needle 12 is moved to the extended position (as shown in FIG. 6). The end wall 19 of the distal portion 16 is adhered to the patient's skin and therefore when the needle 12 is moved to the extended position the needle 12 enters the injection site of the patient.

When the needle 12 is moved to the extended position the needle 12 is fluidly communicated with the inside of the flexible bag 23. In one embodiment, a conduit (not shown) is provided that is fluidly communicated with the inside of the flexible bag 23. The needle 12 comprises an aperture (not shown) that aligns with the conduit to fluidly communicate therewith when the needle 12 is moved to the extended position such that medicament is able to flow out of the flexible bag 23, through the conduit, and into the aperture of the needle 12 to be dispensed from the needle 12. The conduit may fluidly communicate with an outlet (not shown) provided towards the second end 23B of the flexible bag 23.

Figure 9:
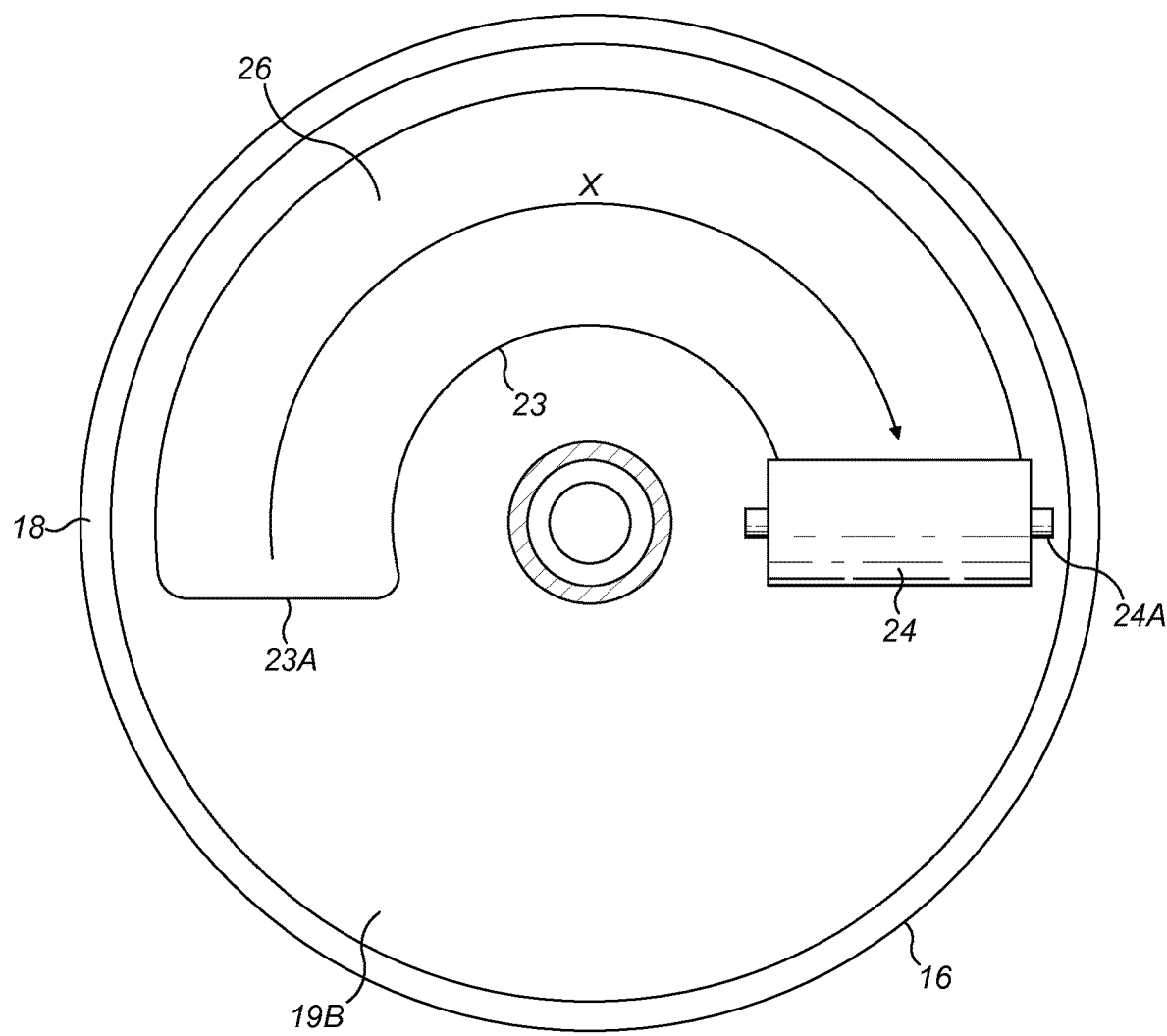
FIG. 9 is a schematic top view of the distal portion of the medicament delivery device of FIG. 1, wherein the roller is located at a second end of the flexible bag; and, FIGS. 10 and 11 are schematic cross-sectional side views of the medicament delivery device of FIG. 1, wherein the needle is in the retracted position.

The patient continues to push the button 15 into the housing 11 to then engage the button 15 with the dispensing lock such that, after the needle 12 has been moved to the extended position, the spiral spring 25 is released to urge the roller 24 along the arcuate path X relative to the distal portion 16 of the housing 11 (as shown in FIGS. 7 and 9). This causes the roller 24 to move over the wall 26 of the flexible bag 23 from the first end 23A to the second end 23B of the flexible bag 23 such that the wall 26 deforms to increase the pressure of the medicament in the flexible bag 23. This causes medicament to be dispensed from the flexible bag 23. More specifically, the distal end of the button 15 is urged against the projection of the dispensing locking member, resulting in the dispensing locking member rotating from the locked state to the unlocked state such that the dispensing locking member is moved away from the roller 24. As discussed above, this allows the roller 24 to move across the wall 26 of the flexible bag 23 under the force of the spiral spring 25. Therefore, the flexible bag 23 is compressed between the roller 24 and the end wall 19 of the distal portion 16 such that the pressure of the medicament in the flexible bag 23 is increased to cause the medicament to flow towards the second end 23B of the flexible bag 23. The medicament flows out of the flexible bag 23 and through the needle 12 to enter the injection site of the patient.

Once the button 15 has been depressed to the extent that the dispensing locking member is moved to the unlocked state to commence medicament delivery, the patient may stop pressing the button 15. The roller 24 will continue to move towards the second end 23B of the flexible bag 23 such that medicament is delivered to the injection site of the patient via the needle 12. Therefore, the medicament delivery device 10 may be used to deliver medicament to the injection site of the patient over an extended time period, for example, several hours, without requiring the patient to continuously apply a force to the button 15.

Figure 10:
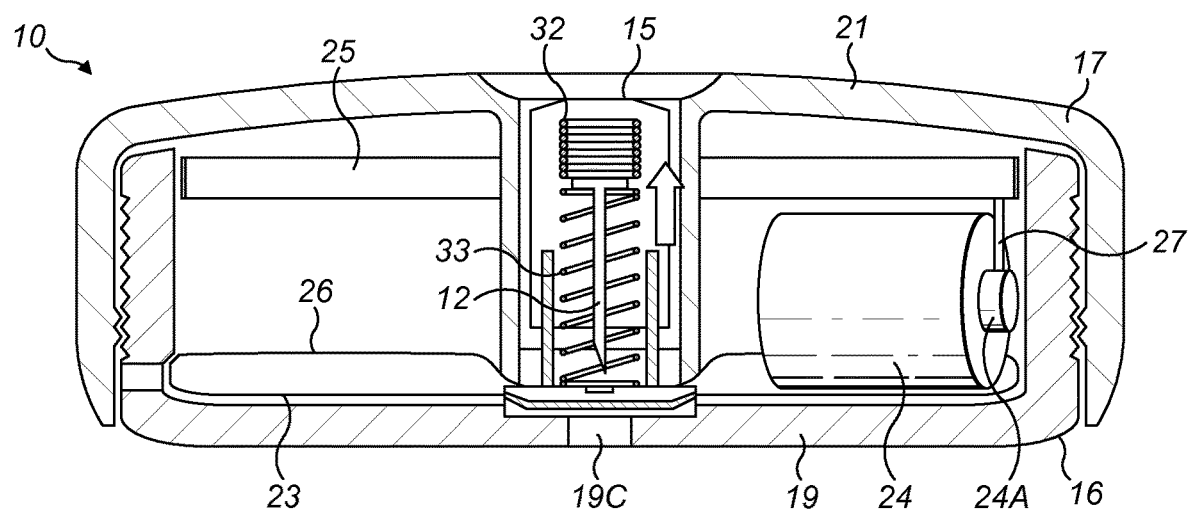
Figure 11:
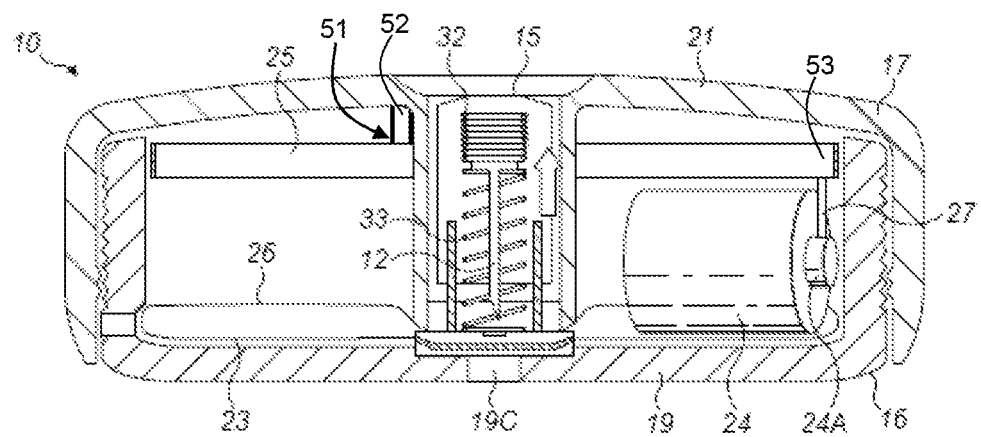

Medicament will continue to be delivered to the injection site until the roller 24 reaches the second end 23B of the flexible bag 23 and engages with the needle retraction lock such that the needle retraction spring 33 is released to move the needle 12 to the retracted position. In more detail, the roller 24 is moved towards the second end 23B of the flexible bag 23 by the force of the spiral spring 25 until the roller 24 is urged against the free end of the first elongate member of the retraction locking member 42, resulting in the retraction locking member rotating from the locked state to the unlocked state. As discussed above, this allows the retraction holding element 35 to move away from the end wall 19 of the distal portion 16 under the force of the needle retraction spring 33 such that the retraction holding element 35 is urged against the base 12A of the needle 12 to move the needle 12 into the housing 11 to the retracted position (as shown in FIG. 10). The patient may then remove the medicament delivery device 10 from the injection site.

In an alternative embodiment, one of the first and second screw threads 62, 63 is omitted and is replaced by a protrusion (not shown) that engages with the other one of the first and second screw threads 62, 63.

In one embodiment (not shown), an actuator lock may be provided to lock the button 15 in position when the proximal portion 17 is in the initial position. The actuator lock may comprise a actuator locking member that is in a locked state when the proximal portion 17 is in the initial position to prevent movement of the button 15 relative to the housing 11. The actuator locking member is moved to an unlocked state when the proximal portion 17 is moved to the primed position such that the button 15 can be moved relative to the housing 11.

In the above described embodiment, the proximal portion 17 is rotated relative to the distal portion 16 of the housing 11 to coil the spiral spring 25 such that a biasing force is exerted on the dispensing member 24. However, in an alternative embodiment (not shown), the spiral spring 25 is pre-coiled and therefore the patient does not need to rotate the proximal portion 17 relative to the distal portion 16 to exert a biasing force on the dispensing member 24. In one such embodiment, the distal and proximal portions 16, 17 of the housing 11 are fixed relative to each other, and may be integrally formed.

In the above described embodiment, the flexible bag 23 extends approximately 180 degrees about the central axis A-A of the housing 11. However, it should be recognised that the flexible bag 23 may extend a different angle about the central axis A-A of the housing 11, for example, 45 degrees or 360 degrees.

Although in the above described embodiment the reservoir 23 comprises a flexible bag 23, in alternative embodiments (not shown) the reservoir 23 may have a different configuration. For example, the reservoir may instead comprise a rigid container with a flexible wall at one end, wherein the dispensing member is arranged to move across the flexible wall to deform the flexible wall such that medicament is dispensed from the reservoir. In another embodiment, the edges of a flexible wall of material are secured to the inner surface 19B of the end wall 19 of the distal portion 16 such that a space is formed between the flexible wall and the inner surface 19B. The space forms a reservoir for medicament. The dispensing member is moved across the flexible wall to increase the pressure in the reservoir such that medicament is dispensed from the reservoir.

In the above described embodiment the dispensing member 24 comprises a roller 24. However, it should be recognised that the roller 24 may be omitted such that the dispensing member 24 does not roll about a second central axis B-B relative to the housing 11. In one such embodiment (not shown), the dispensing member is instead fixed relative to the connecting member 27 such that the dispensing member instead slides across the wall 26 of the flexible bag 23 under the force of the dispensing biasing member 25.

In the above described embodiment, the needle 12 is moveable relative to the housing 11 between the retracted and extended positions. However, in an alternative embodiment the needle 12 is fixed in the extended position such that the needle 12 permanently projects from the housing 11. Thus, when the end wall 19 of the distal portion 16 is secured to the patient's skin the needle 12 pierces the skin to enter the injection site of the patient.

In the above described embodiment, the dispensing lock is mechanically operated, the end of the button 15 being urged against the dispensing locking member to rotate the dispensing locking member from the locked state to the unlocked state. However, in an alternative embodiment the dispensing lock is electrically operated. For example, the dispensing lock may comprise an electromagnetic latch (not shown) that holds the roller 24 in position relative to the distal portion 16 of the housing 11. When the button 15 is depressed by the patient the electromagnetic latch changes state such that the roller 24 is released to move along an arcuate path X relative to the housing 11. Similarly, the needle actuating mechanism may instead be electrically operated, for example comprising a motor (not shown) that moves the needle 12 between the retracted and extended positions.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds.

For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyhepta↔decanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the embodiments discussed herein include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

The invention claimed is:

1. A medicament delivery device comprising:
a housing having a distal end;
a needle configured to project from the distal end of the housing, wherein the distal end of the housing is configured to overlie an injection site of a patient;
a reservoir disposed in the housing and having a flexible wall;
a dispensing member disposed in the housing; and
a biasing member configured to bias the dispensing member to move in an arcuate path relative to the housing such that the dispensing member moves across the flexible wall of the reservoir to dispense medicament from the reservoir when the reservoir contains medicament,
wherein the housing comprises a substantially flat external portion that at least in part defines the distal end such that the substantially flat external portion is configured to lay substantially flat against the injection site, wherein the substantially flat external portion comprises an opening, and wherein the needle is configured to project from the substantially flat external portion through the opening.

2. The medicament delivery device according to claim 1, wherein the dispensing member comprises a roller.

3. The medicament delivery device according to claim 2, wherein the roller is configured to move along the arcuate path relative to the housing about a first rotational axis and is configured to roll about a second rotational axis that is at an angle to the first rotational axis.

4. The medicament delivery device according to claim 1, wherein the reservoir comprises a flexible bag.

5. The medicament delivery device according to claim 1, wherein the biasing member comprises a spiral spring or a torsion spring.

6. The medicament delivery device according to claim 1, wherein the housing comprises first and second portions that are rotatably coupled.

7. The medicament delivery device according to claim 6, wherein rotation of the first portion relative to the second portion resiliently deforms the biasing member such that the biasing member urges the dispensing member to move along the arcuate path relative to the housing.

8. The medicament delivery device according to claim 7, wherein a first end of the biasing member is attached to the first portion of the housing and a second end of the biasing member is coupled to the dispensing member.

9. The medicament delivery device according to claim 6, wherein at least one of the first and second portions comprises a screw thread.

10. The medicament delivery device according to claim 1, wherein the needle is moveable between a retracted position in which it is fully disposed within the housing and an extended position in which is projects from the distal end of the housing to inject the patient's skin in use.

11. The medicament delivery device according to claim 1, further comprising a lock that is movable from a locked state, wherein the biasing member is prevented from moving the dispensing member along the arcuate path relative to the housing, and an unlocked state, wherein the biasing member is able to move the dispensing member along the arcuate path.

12. The medicament delivery device according to claim 1, further comprising a flat surface, wherein the reservoir is compressed between the dispensing member and the flat surface when the dispensing member moves along the arcuate path.

13. The medicament delivery device according to claim 1, wherein the distal end of the housing comprises an adhesive layer to attach the distal end to the patient's skin in use.

14. The medicament delivery device according to claim 1, wherein the reservoir contains medicament.

15. The medicament delivery device according to claim 1, wherein the medicament delivery device is a large volume device.

16. A method of dispensing medicament from a medicament delivery device, the medicament delivery device comprising a housing comprising a substantially flat external portion that at least in part defines a distal end of the housing and that comprises an opening, a needle that is configured to project from the substantially flat external portion through the opening, a dispensing member disposed in the housing, a biasing member disposed in the housing, and a reservoir disposed in the housing and having a flexible wall,
wherein the method comprises:

positioning the substantially flat external portion of the housing substantially flatly against an injection site of a patient, wherein the needle projects from the substantially flat external portion into the injection site; and releasing the biasing member to exert a force on the dispensing member such that the dispensing member moves in an arcuate path relative to the housing across the flexible wall of the reservoir to dispense medicament from the reservoir to the injection site through the needle.

* * * * *